United States Patent [19]

Rieger et al.

[11] 3,979,400

[45] Sept. 7, 1976

[54] PRODUCTION OF PYRIDYL KETONES

[75] Inventors: William H. Rieger; Ernest W. Crowe, both of Indianapolis, Ind.

[73] Assignee: Reilly Tar & Chemical Corporation, Indianapolis, Ind.

[22] Filed: Dec. 11, 1974

[21] Appl. No.: 531,555

[52] U.S. Cl. ............................................. 260/297 R
[51] Int. Cl.$^2$ ...................................... C07D 213/50
[58] Field of Search ................................ 260/297 R

[56] References Cited
UNITED STATES PATENTS

| | | | |
|---|---|---|---|
| 3,075,989 | 1/1963 | Godin et al. | 260/297 R |
| 3,118,899 | 1/1964 | Cislak | 260/297 R |

OTHER PUBLICATIONS

Klingsberg, Pyridine and Its Derivatives, Part Four, frontispage and p. 145, Interscience Publishers (1964).

*Primary Examiner*—John D. Randolph
*Attorney, Agent, or Firm*—Jenkins, Hanley & Coffey

[57] ABSTRACT

Pyridyl ketones are produced from substituted pyridines containing at least one lower alkyl group or arylmethylene group connected to a carbon of the pyridine nucleus by a methylene radical of such group, by air oxidizing the pyridine in the liquid phase at elevated temperature, e.g., 200° C., and pressure, e.g., 400 psig. The reaction is preferably carried out in the presence of an inorganic oxidation catalyst, such as a heavy metal or oxide or hydrated oxide or inorganic salt thereof, but with some pyridines, especially 2-substituted and 4-substituted pyridines, reaction occurs without a catalyst. The reaction mixture is fractionated to recover the pyridyl ketone and unreacted starting material.

20 Claims, No Drawings

PRODUCTION OF PYRIDYL KETONES

BACKGROUND OF THE INVENTION

This invention relates to the production of pyridyl ketones from corresponding substituted pyridines containing at least one alkyl or aralkyl substituent joined to a carbon of the pyridine nucleus by a methylene radical of such substituent, by oxidation of the pyridine in liquid phase with air or other oxygen-containing gas, to convert the methylene radical to a carbonyl radical.

The pyridyl ketones produced by the present invention are in general known compounds which have previously been produced by chemical oxidation, as with potassium permanganate, or by condensation reactions such as the Claisen condensation. Such prior methods of production are relatively laborious and expensive, and the present invention provides an improved method for producing these ketones.

It has previously been proposed to oxidize lower alkyl-substituted pyridines to corresponding pyridine carboxylic acids with oxygen or air in the presence of a catalyst or oxidizing reagent. In general, these proposals use different reagents and reaction conditions and produce acids instead of the pyridyl ketones produced by the present invention.

Hanotier-Bridoux U.S. Pat. No. 3,833,599 is directed to oxidation of alkyl pyridines to corresponding carboxy pyridines, but in its Example 5 reports that oxidation of 4-ethylpyridine produced 79% of isonicotinic acid and 21% of 4-acetyl pyridine. The process requires large proportions of carboxylic acid as solvent and of a cobaltic salt of an alkanoic acid as catalyst-reagent, and requires chemical separation of the product mixture. In contrast, the present invention cleanly produces the ketone as the substantially exclusive reaction product, free of carboxy acids, and permits product recovery by simple fractionation.

Godin U.S. Pat. No. 3,075,989 reports the oxidation of 2-methyl-5-ethylpyridine to 2-methyl-5-acetylpyridine with molecular oxygen and an organic peroxide or hydroperoxide in a process which for adequate yields requires periodic additions of peroxide over a reaction period ranging up to 24 hours or more. In contrast, the present invention uses inorganic catalysts and produces equivalent or better yields in a fraction of the time.

The pyridyl ketones produced by the present invention have various valuable uses, such as intermediates in the manufacture of pharmaceutical and agricultural products and of plastic polymers, as inhibitors, etc. For example: acetylpyridines are useful as non-complexing compounds for brightening in galvanic zinc baths (German Offen. No. 1,919,305; French Demande No. 2,015,422), and to inhibit the reaction of trichloroethane on aluminum (U.S. Pat. No. 3,444,248); 2-acetylpyridine is used to make the antihistamine doxylamine succinate (JACS 71, 887, 1949); 2-methyl-5-acetylpyridine is reported useful as an intermediate in the preparation of plastics polymers (U.S. Pat. No. 3,075,989); and 2-benzoylpyridine is useful to improve the ultraviolet light stability of high density polyethylene (Canadian Pat. No. 836,635).

In accordance with the invention, the substituted pyridine used as a starting material has at least one substituent which is either a lower alkyl group having from 2 to 8 carbon atoms or an aralkyl group, especially an aryl-methylene group such as phenylmethylene or napthylmethylene, and which is connected to a carbon of the pyridine nucleus through a methylene radical of such group. The pyridine may contain more than one such substituent, for example, as in 2,5-diethylpyridine. It may contain other hydrocarbon substituents, such as an alkyl group which is not joined to the nucleus by an oxidizable methylene radical, for example, the methyl substituent in 2-methyl-5-ethylpyridine. The pyridine may also contain other substituents which do not interfere with the desired oxidation, as for example a chloro or nitro substituent on another carbon of the nucleus.

The starting material may be represented as a compound of the formula:

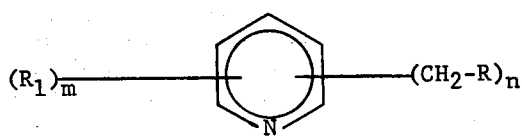

in which
R represents an alkyl group of from 1 to 7 carbon atoms, or an aryl group,
$R_1$ represents a lower alkyl group or hydrogen or a non-oxidizable inorganic substituent such as $-NO_2$, $-SO_3H$, or halogen,
n is an integer of 1 to 5, and
m is zero or an integer of 1 to 4.

The substituted pyridine starting material is subjected to oxidizing reaction conditions at elevated temperatures and under sufficient pressure to maintain liquid phase conditions. The reaction mixture preferably does not contain a solvent as such, and especially not a carboxylic acid solvent such as acetic acid, but may desirably contain a minor amount of vapor pressure additive. A catalyst is desirably present, although with some pyridines and under some conditions, reaction will occur without an added catalyst, especially with 2- and 4-substituted pyridines. The desired oxidation reaction is produced by causing intimate mixing of air or other oxygen-containing gas with the liquid phase reaction mixture containing the pyridine starting material and the catalyst, if present, and such mixing is continued until oxygen uptake has ceased or substantially ceased, as indicated by tests of the gas outflow. The airflow is then stopped and the reaction mixture cooled.

The pyridyl ketone formed in the reaction mixture is conveniently recovered by fractional distillation. Such distillation usually also yields a quantity of the unreacted pyridine starting material which can be reused in subsequent reactions, and may yield more or less of a tarry residue. While a batch process is described, it will be understood that the invention is also unable in a continuous process.

The reaction may be carried out in a closed vessel adapted to be heated and pressurized, fitted with an inlet and an outlet for oxidizing gas, and with a stirring device. We have carried out the process both in glass equipment and in stainless steel equipment.

The temperature of the reaction mixture should be high enough to produce the desired oxidation reaction. Higher temperatures increase the rate of oxidation and yield of desired product, but excessive temperatures may cause destructive oxidation of the materials present and produce increased amounts of tarry residue. The optimum temperature or temperature range to be used will depend on the catalyst used, on the pressure, and on the particular pyridine being oxidized. In general, we have found it convenient to use a temperature of about 200° C. in investigative runs, and have found that temperature to produce effective results, but variations therefrom may be found best for particular operations. For 2-benzyl- and 4-benzyl-pyridines, we consider that the temperature should be at least about 100° C. Alkyl pyridines generally require higher minimum temperatures for reaction, not less than about 170° C. Higher temperatures may be used in any case, and the maximum is in part a matter of convenience but also to avoid degradation of the reactants. In general, we prefer to use temperatures up to about 300° C.

The pressure in the reaction chamber should be sufficient to maintain liquid phase conditions at the prevailing temperature. Higher pressures increase the solubility and concentration of the oxidizing gas in the liquid phase reaction mixture and hence increase the rate of reaction. The pressure to be used varies with the temperature and with the particularly pyridine being oxidized. 2-benzyl- and 4-benzyl-pyridines which have boiling points of 276° and 287° C., respectively, will oxidize at atmospheric pressure at 200° C., but higher pressures are desirably used. Alkyl pyridines require elevated pressures, i.e., above atmospheric pressure. With them we prefer to use a pressure of at least about 150 psig. The maximum pressure used is largely a matter of convenience and safety, and depends on the equipment being used and on the desired rate of reaction. Pressures may range upward to 1000 psig or higher, but in general we prefer to use pressures not more than about 1000 psig. With the foregoing guide lines, the person skilled in the art can readily determine the temperature and pressure to be used in any particular application.

The reaction mixture is desirably composed substantially entirely of the substituted pyridine to be oxidized, and a solvent or diluent is desirably not used. In particular, the reaction mixture desirably does not contain a carboxylic acid as a solvent or otherwise, since such acids react with other components and interfere with clean fractionation to recover the desired reaction product. The mixture may, however, contain a small proportion of a vapor pressure additive, such as water or benzene, which has a lower boiling point than the pyridine, and which is inert and not reactive under the reaction conditions. The amount of such additive will depend on the operating conditions, especially the temperature and pressure being used. The presence of such vapor pressure additive facilitates the use of higher reaction pressures, and is especially advantageous to enhance safety of operation by changing the vapor mixture in the reaction vessel to one outside an explosive range. The amount of additive should not be so great as to significantly dilute the pyridine, and preferably is in the range from none up to about 10% of the amount of pyridine used.

The oxidizing gas used is most conveniently air, but other oxygen-containing gases or gas mixtures may be used, such as air fortified with extra oxygen or diluted with nitrogen or other inert gas. Any such mixture desirably contains only a minor proportion of oxygen, say from about 10% to about 30% oxygen. As with other operating conditions, the optimum oxygen content of the oxidizing gas will vary with other conditions of the reaction and with the particular pyridine being oxidized. Some compounds will undergo the desired reaction with, and withstand, stronger oxidizing conditions than others, while others will give good yields and cleaner results with milder conditions. In general, we prefer to use only sufficiently strong oxidizing conditions as will give satisfactory yields of the desired ketones, and thus to avoid further oxidation as to carboxylic acids and to minimize danger of degradative reactions.

The presence of a catalyst is usually preferred and is in some cases essential. With 2-benzyl- and 4-benzyl-pyridines the desired oxidation reaction was carried out with useful yields in the absence of a catalyst and at atmospheric pressure in glass equipment. With 2-ethyl- and 4-ethylpyridines, the desired oxidation reaction was carried out with good yields in the absence of a catalyst. With such ethylpyridines, the reaction was carried out at elevated pressure and in stainless steel equipment composed of an alloy identified as AISI 316.

A wide variety of catalysts have been found operative. Different catalysts produce different results with the same starting material, and the same catalyst will produce different results with different starting materials, operating conditions, etc.

Catalysts which may be used for the process of the present invention are in general known inorganic oxidation catalysts or reagents. The useful catalysts include the "heavy metals" and their oxides, hydrated oxides, and inorganic salts. The heavy metals are designated as such in the Periodic Table given on page 632 of Hackh's Chemical Dictionary (Third Edition, 1944, The Blakiston Company, Philadelphia, PA) and include the metals having atomic numbers from 22 (titanium) to 92 (uranium) and falling in Periods IV to VII and in Groups 1b, 2b, 3a, 4a, 4b, 5b, 6b, 7b, and 8 of the Periodic Table of Elements as set forth in the CRC Handbook of Chemistry and Physics, 50th Ed., 1969.

Such heavy metals which may be used, either as such or as oxides or hydrated oxides or inorganic salts thereof, include specifically the metals vanadium, chromium, manganese, iron, cobalt, nickel, copper, zinc, molybdenum, palladium, tin, tungsten, platinum, mercury, and uranium.

Other elements which are useful in the same forms as the heavy metals are magnesium, arsenic, and selenium. Still other materials which have been found useful as catalysts comprise sulphur and ammonium bromide.

By inorganic salts we mean to include compounds in which the metal appears in the anion thereof, as in alkali metal salts of chromic or dichromic acid, e.g., $Na_2Cr_2O_7$, and also compounds in which the metal appears in the cation thereof, as in nickel sulfate. By hydrated oxides, we mean to include compounds which under reaction conditions may lose a molecule of water to form an oxide as for example tungstic acid ($H_2WO_4$) which may be considered a hydrated form of tungstic oxide ($WO_3$).

The preferred catalysts, which have been found widely useful under various conditions and are readily available commercially comprise:
1. Manganese compounds, especially manganese dioxide ($MnO_2$)
2. Chromium compounds, especially sodium and potassium dicromates ($Na_2Cr_2O_7$ and $K_2Cr_2O_7$)
3. Vanadium compounds, especially vanadium pentoxide ($V_2O_5$)

The amount of catalyst used can vary over a wide range, and depends on the particular catalyst used, the pyridine being oxidized, and the reaction conditions. If too little is used, yields will be low or non-existent. On the other hand, too much catalyst can cause excessive oxidation and degradation of the starting compound and the desired product, so that the reaction product will be a useless tarry mixture. In any event, the amount used is a "catalytic amount" as distinguished from a chemically "equivalent amount" and is very much smaller than a chemically equivalent amount. Useful amounts may be as little as 0.01% by weight of the amount of pyridine being treated and may be as much as 5% by weight of the pyridine.

The following Examples show different applications and variations of the process. They are given for purposes of illustration only and are not intended to limit the scope of the invention.

In the Examples, where sodium dichromate was used, it was used as the dihydrate ($Na_2Cr_2O_7 \cdot 2H_2O$). Potassium dichromate was also used as the dihydrate ($K_2Cr_2O_7 \cdot 2H_2O$). Proportions given are in all cases by weight.

EXAMPLE 1

The reaction vessel was a 1-liter autoclave attached to a pressurized air source and to a condenser capable of being pressurized. The autoclave was fitted with a magnetically-driven stirring device and a heating mantle. To the autoclave were charged 428 grams (4 mols) of 4-ethylpyridine and 3.0 grams of manganese dioxide (commercial $MnO_2$ powder) as catalyst. The autoclave and reaction mixture were heated to 225° C. and pressurized to 245 psig. Air flow was then set up through the system and periodic tests were made of the percent oxygen in the outgas. When such tests indicated that oxygen uptake had ceased or nearly ceased, the airflow was stopped and the autoclave was cooled to room temperature. The reaction mixture was removed and fractionated by vacuum distillation. On one run for 1 hour and 45 minutes a yield of 198.5 grams of 4-acetylpyridine was obtained, 171.9 grams of 4-ethylpyridine was recovered, and there was a tarry residue of 64.8 grams. The 4-acetylpyridine obtained represented a yield of 68%, based on the amount of 4-ethylpyridine consumed. A second rum for 2 hours gave similar results.

Various other runs with 4-ethylpyridine were carried out, using manganese dioxide catalyst from different sources and from previous runs, with pressures ranging from 175 psig to 410 psig, and with temperatures ranging from 165° to 270° C., and extending for different time periods from 1 hour to 7 hours. In some runs at higher pressures and temperatures about 4.3 grams of water (1% of the pyridine) was added as a vapor-pressure additive in the reaction mixture.

All runs were found to be operative to produce 4-acetylpyridine in yields ranging from about 30% to about 70%, and to permit recovery of substantial quantities of starting material, and to give varying small quantities of residue.

EXAMPLE 2

Additional oxidations of 4-ethylpyridine to 4-acetylpyridine were carried out in the same manner as in Example 1, using 428-gram charges of the pyridine but using different catalysts. The catalysts and conditions used and the results obtained are shown in the following table:

| Catalyst & Amount | Pressure Temp. Time | 4-Acetyl Pyridine Obtained (grams) (% Yield) | 4-Ethyl Pyridine Recovered (grams) | Residue (grams) |
|---|---|---|---|---|
| Sodium Dichromate 1.3 grams | 250 psig 200°C. 6:35 hrs. | 145.9 (49.7%) | 168.5 | 81.7 |
| Sodium Dichromate 5.2 grams | 400 psig 500°C. 5:55 hrs. | 152.9 (40.9%) | 97.6 | 90.9 |
| Nickel Sulfate ($NiSO_4$) 1 gram | 400 psig 200°C. 3:20 hrs. | 165.9 (65.0%) | 176.7 | 65.2 |
| Zinc Oxide (ZnO) 1 gram | 400 psig 200°C. 2:40 hrs. | 99.9 (61.1%) | 283.0 | 56.6 |
| Platinum Dioxide ($PtO_2$) 1 gram | 400 psig 200°C. 4:30 hrs. | 208.6 (67.1%) | 152.9 | 92.6 |
| No Catalyst (Stainless Autoclave) | 400 psig 200°C. 4:00 hrs. | 164.1 (60.1%) | 186.8 | 96.1 |

EXAMPLE 3

Oxidations of 2-ethylpyridine to 2-acetylpyridine were carried out in the manner described in Example 1, using various catalysts in varying amounts, using different conditions and obtaining results as shown in the following table:

| Catalyst & Amount | Pressure Temp. Time | 2-Acetyl Pyridine Obtained (grams) (% Yield) | 2-Ethyl Pyridine Recovered (grams) | Residue (grams) |
|---|---|---|---|---|
| Manganese Dioxide ($MnO_2$) 3 grams | 400 psig 200°C. 5:30 hrs. | 25.6 (26.3%) | 342.0 | 26.3 |
| Sodium Dichromate 1.3 grams | 400 psig 200°C. 5:43 hrs. | 109.9 (76.1%) | 300.3 | 12.7 |
| Sodium Dichromate 2.6 grams | 250 psig 200°C. 4:52 hrs. | 108.6 (78.8%) | 306.4 | 10.4 |
| Sodium Dichromate 20.6 grams | 250 psig 200°C. 3:50 hrs. | 82.6 (46.8%) | 271.6 | 7.5 |
| Potassium Dichromate 5 grams | 400 psig 200°C. 6:35 hrs | 123.8 (61.4%) | 249.7 | 12.8 |
| Ferric Oxide ($Fe_2O_3$) 5.4 grams | 250 psig 200°C. 2:35 hrs. | 16.8 (23.9%) | 367.7 | 13.5 |
| Selenium Dioxide ($SeO_2$) 1 gram | 400 psig 200°C. 5:25 hrs. | 65.6 (42.4%) | 291.4 | 37.0 |
| Titanium Dioxide ($TiO_2$) 1 gram | 400 psig 200°C. 5:25 hrs. | 73.0 (48.7%) | 295.6 | 17.6 |
| Chromium Trioxide ($CrO_3$) 1.7 grams | 400 psig 200°C. 4:26 hrs. | 77.2 (83.2%) | 345.9 | 11.6 |
| Zinc Oxide (ZnO) 1 gram | 400 psig 200°C. 4 hrs. | 48.9 (61.2%) | 356.9 | 13.9 |
| Magnesium Oxide (MgO) 1 gram | 400 psig 200°C. 5:25 hrs. | 69.6 (63.0%) | 329.9 | 14.1 |
| Molybdenum Dioxide ($MoO_2$) 1 gram | 400 psig 200°C. 4:45 hrs. | 37.1 (31.9%) | 324.6 | 20.4 |
| Arsenous Oxide ($As_2O_3$) | 400 psig 200°C. 4:20 hrs. | 33.8 (57.0%) | 375.5 | 11.1 |

| Catalyst & Amount | Pressure Temp. Time | 2-Acetyl Pyridine Obtained (grams) (% Yield) | 2-Ethyl Pyridine Recovered (grams) | Residue (grams) |
|---|---|---|---|---|
| 1 gram Mercuric Oxide (HgO) | 400 psig 200°C. 6 hrs. | 51.9 (51.6%) | 338.9 | 14.0 |
| 1 gram Platinum Dioxide (PtO₂) | 400 psig 200°C. 6:15 hrs. | 62.4 (53.2%) | 324.0 | 19.7 |
| 1 gram Nickelous Nitrate [Ni(NO₃)₂] | 400 psig 200°C. 6:20 hrs. | 57.6 (60.8%) | 343.4 | 15.1 |
| 1 gram Cobalt Sulfate (CoSO₄) | 400 psig 200°C. 3:15 hrs. | 24.4 (77.5%) | 399.8 | 13.2 |
| 1 gram Uranium Nitrate [UO₂(NO₃)₂] | 400 psig 200°C. 6:30 hrs. | 49.1 (59.7%) | 355.2 | 16.1 |
| 2 grams Tungstic Acid (H₂WO₄) | 400 psig 200°C. 4:50 hrs. | 53.3 (45.5%) | 324.4 | 21.1 |
| 2 grams Palladium on Carbon (Pd/C) | 400 psig 200°C. 6:20 hrs. | 88.2 (68.1%) | 313.9 | 14.7 |
| 2 grams Sulfur (S) 1 gram | 400 psig 200°C. 6:15 hrs. | 61.5 (37.6%) | 283.8 | 17.4 |
| Tin (Sn.) 1 gram | 400 psig 200°C. 3:50 hrs. | 48.4 (80.0%) | 374.0 | 9.6 |
| Ammonium Bromide (NH₄Br) 1 gram | 400 11.1 200°C. 6:15 hrs. | 43.0 (39.5%) | 331.6 | 27.6 |
| No Catalyst Stainless Auto- (a) clave 5 runs | 400 psig 200°C. 6 hrs. | 59.6 (60.8%) | 314.4 | 10.7 |
| (b) | 6:30 hrs. | 67.2 (70.3%) | 343.9 | 10.6 |
| (c) | 7:10 hrs. | 78.1 (62.8%) | 317.0 | 23.5 |
| (d) | 5:57 hrs. | 63.8 (86.4%) | 362.9 | 1.1 |
| (e) | 3:00 hrs. | 50.0 (83.8%) | 375.2 | 9.4 |

EXAMPLE 4

Oxidation of 2-ethylpyridine to 2-acetylpyridine was carried out in the manner described in Example 1, using 428 grams of 2-ethylpyridine and different amounts of the same catalyst, namely, vanadium pentoxide ($V_2O_5$). In each run the reaction pressure was 250 psig and the temperature was 200° C. The amounts of catalyst used and the results obtained were as follows:

| Vanadium Pentoxide (grams) | Reaction Time | 2-Acetyl Pyridine Obtained (grams) (% Yield) | 2-Ethyl Pyridine Recovered (grams) | Residue (grams) |
|---|---|---|---|---|
| 0.055 | 5:45 hrs. | 88.7 (51.7%) | 277.9 | 27.2 |
| 0.2 | 5:12 hrs. | 75.3 (50.1%) | 283.2 | 23.8 |
| 0.5 | 5:25 hrs. | 74.7 (40.8%) | 264.7 | 26.1 |
| 0.8 | 4:32 hrs. | 66.9 (41.0%) | 285.3 | 24.1 |
| 1.5 | 5:32 hrs. | 64.4 (26.2%) | 212.4 | 35.6 |
| 3.1 | 2:00 hrs. | 30.8 (24.0%) | 314.0 | 26.9 |
| 6.2 | 4:12 hrs. | (Only tar recovered) | | |

The results of this series of experiments indicate that the amount of catalyst may be varied over a considerable range, but that excessive amounts can produce degradation and destruction of the reaction compounds.

EXAMPLE 5

Oxidation of 3-ethylpyridine to 3-acetylpyridine was carried out in the manner described in Example 1. The reaction was run at a pressure of 400 psig and a temperature of 200° C., and the reaction time was 3:40 hours. One gram of zinc oxide was used as catalyst. This gave 55.9 grams of 3-acetylpyridine, representing a yield of 52.3%, and 332.9 grams of 3-ethylpyridine was recovered. There was a residue of 23.4 grams.

Three similar runs were carried out except that the catalyst used was 1.3 grams of sodium dichromate dihydrate ($Na_2Cr_2O_7 \cdot 2H_2O$), and the reaction times ranged from 2:30 hours to 3:48 hours. Yields of from 124 to 148 grams of 3-acetylpyridine were obtained, representing yields of 67 to 80%, and from 230 to 280 grams of 3-ethylpyridine was recovered, with a residue of about 26 grams.

A trial run at 225 psig and 225° C. using manganese dioxide ($MnO_2$) as the catalyst produced relatively poor results and a yield of less than 10% 3-acetylpyridine, which indicates that other catalysts are to be preferred for this pyridine.

EXAMPLE 6

Oxidations of 2-n-propylpyridine were carried out in two runs in the manner described in Example 1. The amount of starting material used in each case was 484 grams, and the reactions were both run at a pressure of about 250 psig and a temperature of 200° C. In one run, 3.0 grams of manganese dioxide ($MnO_2$) was used as the catalyst, the reaction time was 2:30 hours, 21.6 grams of ethyl 2-pyridylketone were obtained, representing a yield of 21%, 391 grams of starting material were recovered, and there was a residue of 32.1 grams. In the other run, 1.3 grams of sodium dichromate dihydrate ($Na_2Cr_2O_7 \cdot 2H_2O$) was used as the catalyst, the reaction time was 4:17 hours, 49.0 grams of ethyl 2-pyridylketone were obtained, 311.4 grams of starting material were recovered, and there was a residue of 35.7 grams.

EXAMPLE 7

Example 6 was repeated, except that 4-n-propylpyridine was used instead of 2-n-propylpyridine. In a run with 3.0 grams of manganese dioxide as the catalyst, at a pressure of 240 psig and a temperature of 200° C. for a reaction time of 4:40 hours, 123.0 grams of ethyl 4-pyridylketone were obtained representing a yield of 34.3%, while 184.7 grams of starting material were recovered, and there was a residue of 161.5 grams.

With 1.3 grams of sodium dichromate dihydrate as the catalyst in a run at 250 psig and 200° C. for 2:47 hours, 45.2 grams of ethyl 4-pyridylketone were obtained, representing a yield of about 20%, while 269.3 grams of starting material were recovered, with a residue of 90 grams.

EXAMPLE 8

Oxidation of 2,5-diethylpyridine to 2,5-diacetylpyridine was carried out in the manner set forth in Example 1, in a plurality of runs. In each run, the charge of starting material was 540 grams, the catalyst used was 1.3 grams of sodium dichromate dihydrate, and the temperature used was 200° C. In one run at 400 psig for a reaction time of 6:20 hours, 83.4 grams of 2,5-diacetylpyridine were obtained, representing a yield of 17.7%, and 149.2 grams of starting material were recovered. In a second run at 250 psig for a reaction time of 5 hours, 24.5 grams of 2,5-diacetylpyridine were obtained, and 279.8 grams of starting material were recovered.

EXAMPLE 9

The second run of Example 8 was repeated except that 3,4-diethylpyridine was used as the starting material. A yield of 106 grams of 3-ethyl-4-acetylpyridine was obtained, representing a yield of 35.1%, 265 grams of starting material was recovered, and there was a residue of 106 grams.

EXAMPLE 10

Oxidation of 2-methyl-5-ethylpyridine was carried out in several runs in the manner described in Example 1 using charges of 484 grams, using in each case a pressure of 400 psig and a temperature of 200° C. The catalysts used and the results obtained are shown in the following table:

| Catalyst & Amount | Time | 2-Methyl-5-Acetyl Pyridine (grams) (% Yield) | Starting Material Recovered (grams) | Residue (grams) |
|---|---|---|---|---|
| Sodium Dichromate 1.3 grams | 6:20 hrs. | 79.5 (23.4%) | 186.1 | 122.1 |
| Sodium Dichromate 1.3 grams | 2:54 hrs. | 113.2 (49.6%) | 280 | 44.3 |
| Selenium Dioxide (SeO$_2$) 1 gram | 3:52 hrs. | 21.2 (11.6%) | 320.2 | 106.0 |
| Ferric Oxide (Fe$_2$O$_3$) 1 gram | 3:20 hrs. | 88.2 (45.7%) | 308.9 | 57.7 |
| Cupric Oxide (CuO) 1 gram | 4:00 hrs. | 13.0 (6.6%) | 300.2 | 113.0 |
| Vanadium Pentoxide (V$_2$O$_5$) 1 gram | 3:50 hrs. | 17.4 (7.9%) | 284.5 | 67.1 |

EXAMPLE 11

Oxidations of 4-benzylpyridine to 4-benzoylpyridine were carried out as described in Example 1, in several runs. The catalysts used, the reaction pressures, temperatures and times, and the results obtained are shown in the following table. In all runs, charges of 422.5 grams of starting material was used.

| Catalyst & Amount | Pressure Temp. Time | 4-Benzyl Pyridine Obtained (grams) (% Yield) | Starting Material Recovered (grams) | Residue (grams) |
|---|---|---|---|---|
| Manganese Dioxide (MnO$_2$) 3 grams | 250 psig 200°C. 6 hrs. | 379.9 (83.0%) | None | 14.8 |
| Same | 5:20 hrs. | 365.9 (80.0%) | None | 18.1 |
| Sodium Dichromate 1.3 grams | 250 psig 200°C. 4:30 hrs. | 358.0 (89.0%) | 51.0 | 22.5 |
| Cupric Oxide (CuO) 1 gram | 400 psig 200°C. 4:24 hrs. | 416.5 (94.3%) | 13.8 | 11.6 |
| Ferric Oxide (Fe$_2$O$_3$) 1 gram | 400 psig 200°C. 4:13 hrs. | 437.9 (99.3%) | 14.9 | 12.8 |
| Vanadium Pentoxide (V$_2$O$_5$) 1 gram | 400 psig 200°C. 4:00 hrs. | 375.3 (84.4%) | 12.0 | 49.6 |
| Selenium Dioxide (SeO$_2$) 1 gram | 400 psig 200°C. 5:25 hrs. | 364.1 (81.9%) | 11.8 | 60.3 |

EXAMPLE 12

Oxidation of 2-benzylpyridine to 2-benzoylpyridine was carried out as described in Example 1 in several runs. The catalysts used, the reaction pressures, temperatures and times, and the results obtained are shown in the following table. In all runs, charges of 422.5 grams of starting material were used. Twelve runs were made using manganese dioxide with pressures ranging from 240 psig to 280 psig, and temperatures ranging from 175° to 225° C. Yields ranged above 75% except on two runs at temperatures below 200° C. The data on a selected one of the 12 runs is included below.

| Catalyst & Amount | Pressure Temp. Time. | 2-Benzoyl Pyridine Obtained (grams) (% Yield) | Starting Material Recovered (grams) | Residue (grams) |
|---|---|---|---|---|
| Manganese Dioxide (MnO$_2$) 3 grams | 242 psig 200°C. 5:00 hrs. | 393.0 (85.5%) | 0 | 32.7 |
| Sodium Dichromate 1.3 grams | 250 psig 200°C. 2:20 hrs. | 248.3 (83.0%) | 146.0 | 4.8 |
| Vanadium Pentoxide (V$_2$O$_5$) 1 gram | 400 psig 200°C. 7:07 hrs. | 339.2 (74.1%) | 0 | 70.3 |
| Selenium Dioxide (SeO$_2$) 1 gram | 400 psig 200°C. 6:00 hrs. | 334.5 (73.2%) | 0 | 91.1 |
| Ferric Oxide (Fe$_2$O$_3$) 1 gram | 400 psig 200°C. 6:23 hrs. | 299.9 (65.6%) | 0 | 78.4 |
| Cupric Oxide (CuO) 1 gram | 400 psig 200°C. 5:32 hrs. | 297.8 (65.0%) | 0 | 107.7 |

EXAMPLE 13

Oxidations of 2-benzylpyridine and 4-benzylpyridine to corresponding benzoyl pyridines were carried out as in Examples 11 and 12, with the addition of vapor pressure additives to the reaction mixtures. In each run, the charge of the benzyl pyridine was in the amount of 422.5 grams, the catalyst used was 3.0 grams of manganese dioxide ($MnO_2$), and the reaction was carried out at 400 psig and 200° C. The vapor pressure additive and the results obtained are shown in the following tables.

| Vapor Pressure Substance & Amount | Reaction Time | Benzoyl Pyridine Obtained (grams) (% Yield) | Starting Material Recovered grams | Residue (grams) |
|---|---|---|---|---|
| A. 4-Benzylpyridine | | | | |
| Benzene 4.5 grams | 4:33 hrs. | 303.2 (90.2%) | 113.8 | 13.8 |
| Benzene 10 grams | 5:53 hrs. | 337.4 (92.6%) | 86.5 | 11.9 |
| Benzene 10 Water 4 g. | 6:15 hrs. | 350.5 (94.0%) | 77.3 | 11.6 |
| Water 15 grams | 5:50 hrs. | 301.5 (90.4%) | 114.9 | 16.9 |
| Water 25 grams | 6:00 hrs. | 302.9 (90.2%) | 112.8 | 11.1 |
| Water 50 grams | 6:00 hrs. | 323.8 (93.7%) | 103.3 | 11.6 |
| B. 2-Benzylpyridine | | | | |
| Water 25 grams | 6:37 hrs. | 391.9 (88.9%) | 15.0 | 11.8 |
| Water 30 grams | 6:20 hrs. | 354.1 (89.7%) | 51.5 | 6.2 |

EXAMPLE 14

4-benzylpyridine in the amount of 300 grams was charged to a 500 ml. three-necked glass flask fitted with a reflux condenser and a stirring device. The charge was heated to 200° C., and remained at atmospheric pressure. Air was passed through the reaction mixture by means of a gas dispersion tube at a rate of 2 standard liters per minute, while the mixture was stirred. The reaction conditions were continued for a period of about 6 hours and were then terminated and the mixture cooled. Gas chromatography examination of the reaction mixture showed that it contained 18.8% of 4-benzoylpyridine and 79.2% of 4-benzylpyridine. This example shows that oxidation of 4-benzylpyridine to 4-benzoylpyridine occurs at atmospheric pressure and without the presence of a catalyst, and gives a high yield in relation to the amount of starting material consumed. Comparison with Examples 11–13 shows that efficiency improved with the use of a catalyst and elevated pressures.

We claim:

1. The method of producing a pyridyl ketone from a substituted pyridine containing at least one substituent which is a lower alkyl group having from 2 to 8 carbon atoms or an arylmethylene group, connected to a carbon of the pyridine nucleus by a methylene radical of such group, which comprises the steps of heating the substituted pyridine to an elevated reaction temperature of from about 100° C. to about 300° C., without the addition of carboxylic acid, with or without the addition of a minor proportion of an inert vapor pressure additive, with a catalytic amount, not exceeding about 5% by weight of the pyridine, of an inorganic oxidation catalyst, or without any catalyst, maintaining the reaction mixture at a pressure sufficient to maintain liquid phase conditions and cause oxygen-containing gas to go into solution in the liquid phase, mixing a supply of air or other oxygen-containing gas with the heated mixture so as to cause the said methylene group of said substituent in a substantial portion of the substituted pyridine to be oxidized to a carbonyl group, and separating the pyridyl ketone thus formed from the resulting mixture.

2. The method of claim 1 which is carried out with a catalyst of the class consisting of the heavy metals and magnesium and arsenic and selenium, the oxides and hydrated oxides and inorganic salts thereof, and sulfur, and ammonium bromide.

3. The method of claim 2 in which the oxygen-containing gas is air.

4. The method of claim 1 in which the substituted pyridine contains an alkyl or arylmethylene group at the 2-position or the 4-position and the method is carried out without a catalyst.

5. The method of claim 2 in which the catalyst is a vanadium compound.

6. The method of claim 2 in which the catalyst is a chromium compound.

7. The method of claim 2 in which the catalyst is a manganese compound.

8. The method of claim 1 wherein the substituted pyridine is a benzyl pyridine, the temperature is in the range from about 100° C. to about 300° C., and the pressure is in the range from atmospheric pressure to about 1,000 psig.

9. The method of claim 1 wherein the substituted pyridine is an alkyl pyridine, the temperature is in the range from about 170° to about 300° and the pressure is in the range from about 150 psig to about 1,000 psig.

10. The method of claim 2 wherein the substituted pyridine is an alkyl pyridine, the temperature is in the range from about 170° to about 300° and the pressure is in the range from about 150 psig to about 1,000 psig.

11. The method of claim 2 wherein the starting material contains a 2-ethyl substituent and the catalyst is a chromium compound, a cobalt compound, or palladium.

12. The method of claim 2 wherein the starting material contains 3-ethyl substituent and the catalyst is an alkali metal dichromate.

13. The method of claim 2 wherein the starting material contains a 4-ethyl substituent and the catalyst is manganese dioxide.

14. The method of claim 2 wherein the starting material contains a 2-benzyl or 4-benzyl substituent, the temperature is at least about 200° C., and the pressure is at least about 200 psig.

15. The method of claim 14 in which the reaction mixture contains up to 10% of an inert vapor pressure additive.

16. The method of producing a pyridyl ketone from a substituted pyridine containing at least one substituent which is a lower alkyl group having from 2 to 8 carbon atoms or an arylmethylene group, connected to a carbon of the pyridine nucleus by a methylene radical of such group, which comprises heating the substituted pyridine to an elevated temperature of from about 100° C. to about 300° C.,
in the absence of added carboxylic acid,
with a catalytic amount, not exceeding about 5% by weight of the pyridine, of an inorganic oxidation catalyst, or without any catalyst,
maintaining the reaction mixture at a pressure sufficient to maintain liquid phase conditions, and
intimately mixing a supply of air or other oxygen-containing gas with the heated mixture for a time sufficient to cause the methylene group of said substituent in a substantial portion of the pyridine to be oxidized to a carbonyl group.

17. The method of claim 16 in which the substituted pyridine contains a 2-benzyl or 4-benzyl substituent, and which is carried out at a pressure of from atmospheric pressure to 1,000 psig.

18. The method of claim 16 in which the substituted pyridine contains a 2-ethyl or 4-ethyl substituent, and which is carried out at a temperature above about 170° C., and a pressure from about 150 psig to about 1,000 psig.

19. The method of claim 16 in which the substituted pyridine is substituted in the 3 or 5 position, and which is carried out at a temperature from about 170° C. to about 300° C., and a pressure from about 150 psig to about 1,000 psig.

20. The method of claim 16 in which a catalyst is used, and such catalyst is a member of the class consisting of the heavy metals and magnesium and arsenic and selenium, the oxides and hydrated oxides and inorganic salts of said elements, and sulfur and ammonium bromide.

* * * * *

UNITED STATES PATENT OFFICE
CERTIFICATE OF CORRECTION

Patent No. 3,979,400      Dated September 7, 1976

Inventor(s) William H. Rieger and Ernest W. Crowe

It is certified that error appears in the above-identified patent and that said Letters Patent are hereby corrected as shown below:

Column 2, line 55, change "unable" to --usable--.

Column 5, line 44, change "rum" to --run--.

In Example 3 (Column 7), across from "Ammonium Bromide", change "400 11.1" to --400 psig--.

In Example 3 (Column 7), in line (d), change "1.1" to --11.1--.

Signed and Sealed this

Fourteenth Day of December 1976

[SEAL]

Attest:

RUTH C. MASON  
Attesting Officer

C. MARSHALL DANN  
Commissioner of Patents and Trademarks